United States Patent [19]
O'Lenick, Jr.

[11] Patent Number: 6,087,517
[45] Date of Patent: Jul. 11, 2000

[54] FLUORINATED DIMETHICONE COPOLYOL PHOSPHATE

[75] Inventor: Anthony J. O'Lenick, Jr., Dacula, Ga.

[73] Assignee: Phoenix Research Co., Somerville, N.J.

[21] Appl. No.: 09/459,325

[22] Filed: Dec. 13, 1999

[51] Int. Cl.$^7$ ........................................................ C07F 7/08
[52] U.S. Cl. .............................................. 556/405; 528/36
[58] Field of Search ................................. 556/405; 528/36

[56] References Cited

U.S. PATENT DOCUMENTS

| | | |
|---|---|---|
| 5,093,452 | 3/1992 | O'Lenick, Jr. ........................... 556/405 |
| 5,446,144 | 8/1995 | O'Lenick . |
| 5,481,015 | 1/1996 | Nomura ................................... 556/405 |
| 5,627,296 | 5/1997 | Dauth et al. ............................. 556/405 |
| 5,872,272 | 2/1999 | Yano et al. .......................... 556/405 X |

*Primary Examiner*—Paul F. Shaver

[57] ABSTRACT

The invention relates to a series of novel silicone fluorinated dimethicone copolyol phosphates. This class of compounds provides breathable barriers when applied to textiles and paper and by vityue of the anionic group present forms very stable emulsions. These emulsuions allow for delivery of barriers to the skin that allow for the passage of water and air through the barrier, but do not allow for the passage of oils. The compounds of the present invention are prepared by reacting a fluoro dimethicone copolyol disclosed in U.S. Pat. No. 5,446,144 with a suitable phosphating agent.

12 Claims, No Drawings

FLUORINATED DIMETHICONE COPOLYOL PHOSPHATE

BACKGROUND OF THE INVENTION

FIELD OF THE INVENTION

The invention relates to a series of novel silicone fluorinated dimethicone copolyol phosphates. This class of compounds provides breathable barriers when applied to textiles and paper and by vityue of the anionic group present forms very stable emulsions. These emulsuions allow for delivery of barriers to the skin that allow for the passage of water and air through the barrier, but do not allow for the passage of oils. The compounds of the present invention are prepared by reacting a fluoro dimethicone copolyol disclosed in U.S. Pat. No. 5,446,144 with a suitable phosphating agent.

We have unexpectantly found that the incorporation of the phosphate group into the backbone of the silicone molecule results in superior emulsification properties and very effective delivery of the barrier to the skin, when compared to the non-phosphated fluorodimethicone copolyol of U.S. Pat. No. 5,446,114. U.S. Pat. No. 5,446,114 is incorporated herein by reference. The referenced patent states "The presence of (a) silicone backbone, (b) a fluorine containing pendant group and (c) a separate dimethicone copolyol group containing a free polar hydroxyl group is critical to the functionality of the molecule. If the fluorine containing group is lacking in the molecule, the desired impermeability to oil is not achieved. If the polar hydroxyl containing group is lacking in the molecule, the barrier is impermeability to both water and oil. If the fluorine is present in the same pendant group as the hydroxyl group the desired barrier is not achieved. Only when the correct combination of groups are placed in the molecule is the desired material achieved."
We have surprisingly found that if the hydroxyl group thought to be critical to the 5,446,114 invention is replaced by a phosphate group the substantivity and barrier properties are asignifncantly improved. The anonic nature of the pendant group results in improved efficiency over the polar hydroxyl group on skin.

The compounds of the present invention are prepared by reacting the compounds of U.S. Pat. No. 5,446,114 with a suitable phosphationg agent selected from polyphosporic acid and phosphorus pentoxide.

The compounds find application in a variety of applications, most importantly the skin care segment of the personal care market.

ARTS AND PRACTICES

Silicone compounds have been known to be active at the surface of cellulosic and synthetic fibers as well as paper. They are good nondurable lubricants and are very stable to oxidation, however, their high cost and lack of efficiency at low concentrations as well as low durability have made their acceptance in commercial products quite low.

In addition to their high cost, silicone compounds have little or no solubility in mineral oils, fatty triglycerides and other classical fatty quaternary compounds used for softening. This has resulted in the inability to prepare stable blends for use as a textile fiber treatment.

U.S. Pat. No. 5,164,471 issued in October 1992 to O'Lenick teaches that fluoro polyesters of silanols can be prepared by the reaction of a silanol, fluorine containing alcohol and a diacid.

U.S. Pat. No. 5,446,114 to O'Lenick issued in August 1995, discloses the fluoro dimethicone copolyol compounds used as raw materials in the present invention. This invention failed to recognize the added benefits of the phosphate functionality when added to the molecule replacing the hydroxyl functionality.

None of these cited patents teach the incorporation of phosphate group, an alkylene oxide group and a separate fluorine containing group on the silicone backbone necessary to achieve the desired properties of the compounds of the present invention.

THE INVENTION

OBJECT OF THE INVENTION

It is the object of the present invention to provide novel anionic fluorine containing dimethicone copolyols compounds. These materials offer unique barrier properties and are verysubstantive to the skin when applied in aqueous systems.

SUMMARY OF THE INVENTION

The present invention relates to a series of novel fluoro dimethicone copolyol phosphates. The compounds of the present invention are prepared by reacting a series of fluoro dimethicone copolyol compounds disclosed in U.S. Pat. No. 5,446,114, with a suitable phosphating agent like polyphosphoric acid or phosphorus pentoxide.

As will become clear from the disclosure, the compounds of the present invention having silicone present in the molecule, fluorine present and an anionic phosphate group present, all these result in a differentially permeable film and improved skin substantivity.

The compounds of the present invention conform to the following structure;

Terminal Compounds $$R'-\underset{Me}{\underset{|}{Si}}-\left[O-\underset{Me}{\underset{|}{Si}}\right]_p-O-\underset{Me}{\underset{|}{Si}}-R$$

wherein;

p is an integer ranging from 1 to 2,000;

Me is methyl;

R' is $-(CH_2)_3-O-(EO)_a-(PO)_b-(EO)_c-P(O)(OH)_2$ and

R is $-(CH_2)_2-(CF_2)_s-CF_3$;

s is an integer ranging from 1 to 13;

a, b and c are each independently integers ranging from 0 to 20;

EO is $-(CH_2CH_2-O)-$;

PO is a $-(CH_2CH(CH_3)-O)-$.

Comb Compounds $$Me-\underset{Me}{\underset{|}{Si}}-\left[O-\underset{R}{\underset{|}{Si}}\right]_o-\left[O-\underset{Me}{\underset{|}{Si}}\right]_q-\left[O-\underset{R'}{\underset{|}{Si}}\right]_t-O-\underset{Me}{\underset{|}{Si}}-Me$$

wherein;

Me is methyl;

o is an integer ranging from 1 to 20;

t is an integer ranging from 1 to 20;
q is an integer ranging from 0 to 2000;
R' is —(CH$_2$)$_3$—O—(EO)$_a$—(PO)$_b$—(EO)$_c$—P(O)—(OH)$_2$ and
R is —(CH$_2$)$_2$—(CF$_2$)$_s$—CF$_3$;
s is an integer ranging from 1 to 13;
a, b and c are each independently integers ranging from 0 to 20;
EO is —(CH$_2$CH$_2$—O)—;
PO is a —(CH$_2$CH(CH$_3$)—O)—.

Raw Materials

The following examples are taken from U.S. Pat. No. 5,446,114 to O'Lenick issued in August 1995, incorporated herein by reference. They are raw materials for the preparation of the compounds of the present invention.

| Example | U.S. Pat. No. 5,446,114 Example Number |
|---|---|
| 1 | 22 |
| 2 | 23 |
| 3 | 24 |
| 4 | 25 |
| 5 | 26 |
| 6 | 27 |
| 7 | 28 |
| 8 | 29 |
| 9 | 30 |
| 10 | 31 |
| 11 | 32 |
| 12 | 33 |

Preparation of Fluoro Dimethicone Copolyol Phosphate

Phosphating Agents

Polyphosphoric Acid (PPA) is 115% phosphoric acid. When used as a phosphating agent in gives more mono ester than the phosphorus pentoxide.

Phosphorus pentoxide is P$_2$O$_5$. It is more aggressive in phosphation and results in more diester.

The silicone phosphates of this invention can be prepared by reacting the hydroxyl containing silicone polymer with a suitable phosphating agent. Preferred phosphating reagents are polyphosphoric acid and phosphorus pentoxide.

The preparation of the novel silicone phosphates of this invention from the hydroxy silicone compounds can be illustrated by the following reaction in which R is the hydroxy silicone compound.

Phosphation Reaction Sequence

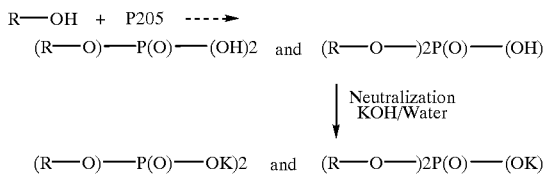

It will be understood by the above reaction that the product of phosphation, weather using polyphosphoric acid or phosphorus pentoxide give a mixture of mono and di ester.

The following examples further illustrate the objects and advantages of this invention, though it should be understood that the various reactants and amounts thereof, reaction conditions, and other details are merely illustrative and should not be construed to unduly limit this invention.

GENERAL PROCEDURE

The specified amount of fluoro hydroxy silicone compound (Examples 1–13) is added to a suitable reaction vessel. The specified amount of either polyphosphoric acid or phosphorus pentoxide is charged to under good agitation over a 2 hr. period. The exothermic reaction raises the temperature of the mixture to about 70° C. After 1 hour slowly raise the temperature to 100° C. and hold 2–4 hours.

| | Phosphorus Pentoxide | | |
|---|---|---|---|
| | Fluoro DMC | | Phosphorus Pentoxide |
| Example | Example | Grams | Grams |
| 27 | 1 | 3673.0 | 36.0 |
| 28 | 2 | 15161.0 | 36.0 |
| 29 | 3 | 149190.0 | 36.0 |
| 30 | 4 | 38408.0 | 36.0 |
| 31 | 5 | 964.0 | 36.0 |
| 32 | 6 | 1107.0 | 36.0 |
| 33 | 7 | 902.0 | 36.0 |
| 34 | 8 | 11056.0 | 36.0 |
| 35 | 11 | 5269.0 | 36.0 |
| 36 | 12 | 1264.0 | 36.0 |
| 37 | 13 | 1492.0 | 36.0 |

The compounds of the present invention are very highly lubricious materials that form thin films and are exceptional emulsifiers for both silicone and alkyl fluoro compounds.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed:

1. A polymer which conforms to the following structure:

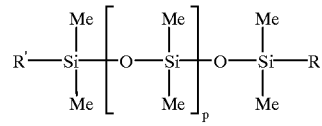

wherein;
is an integer ranging from 1 to 2,000;
Me is methyl;
R' is —(CH$_2$)$_3$—O—(EO)$_a$—(LO)$_b$—(EO)$_c$—P(O)(OH)$_2$ and
R is —(CH$_2$)$_2$—(CF$_2$)$_s$—CF$_3$;
s is an integer ranging from 1 to 13;
a, b and c are each independently integers ranging from 0 to 20;
EO is —(CH$_2$CH$_2$—O)—;
LO is a —(CH$_2$CH(CH$_3$)—O)—.
2. A polymer of claim 1 wherein s is 1.
3. A polymer of claim 1 wherein s is 5.
4. A polymer of claim 1 wherein s is 7.
5. A polymer of claim 1 wherein s is 10.

6. A polymer of claim 1 wherein s is 13.
7. A polymer which conforms to the following structure

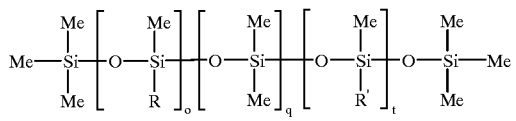

wherein;

Me is methyl;

o is an integer ranging from 1 to 20;

t is an integer ranging from 1 to 20;

q is an integer ranging from 0 to 2000;

R' is —$(CH_2)_3$—O—$(EO)_a$—$(LO)_b$—$(EO)_c$—P(O)—$(OH)_2$ and

R is —$(CH_2)_2$—$(CF_2)_s$—$CF_3$;

is an integer ranging from 1 to 13;

a, b and c are each independently integers ranging from 0 to 20;

EO is —$(CH_2CH_2$—O)—;

PO is a —$(CH_2CH(CH_3)$—O)—.

8. A polymer of claim 7 wherein s is 1.
9. A polymer of claim 7 wherein s is 5.
10. A polymer of claim 7 wherein s is 7.
11. A polymer of claim 7 wherein s is 10.
12. A polymer of claim 7 wherein s is 13.

* * * * *